United States Patent
Zhao et al.

(10) Patent No.: US 12,113,349 B2
(45) Date of Patent: Oct. 8, 2024

(54) HEATING LOOP PROTECTIVE CIRCUIT, RESPIRATION HEATING CIRCUIT AND RESPIRATION AIDING EQUIPMENT

(71) Applicants: VINCENT MEDICAL (DONG GUAN) MANUFACTURING CO., LTD, Guangdong (CN); VINCENT MEDICAL (DONG GUAN) TECHNOLOGY CO., LTD, Guangdong (CN)

(72) Inventors: Jun Zhao, Guangdong (CN); Jiebing Xu, Guangdong (CN); Haibin Yu, Guangdong (CN); Liting Wang, Guangdong (CN)

(73) Assignees: VINCENT MEDICAL (DONG GUAN) MANUFACTURING CO., LTD, Guangdong (CN); VINCENT MEDICAL (DONG GUAN) TECHNOLOGY CO., LTD, Guangdong (CN)

( * ) Notice: Subject to any disclaimer, the term of this patent is extended or adjusted under 35 U.S.C. 154(b) by 0 days.

(21) Appl. No.: 17/802,369

(22) PCT Filed: Dec. 24, 2021

(86) PCT No.: PCT/CN2021/141035
§ 371 (c)(1),
(2) Date: Aug. 25, 2022

(87) PCT Pub. No.: WO2022/193772
PCT Pub. Date: Sep. 22, 2022

(65) Prior Publication Data
US 2024/0022062 A1    Jan. 18, 2024

(30) Foreign Application Priority Data
Mar. 18, 2021   (CN) .......................... 202110290020.7

(51) Int. Cl.
*H02H 3/08* (2006.01)
*A61M 16/10* (2006.01)
(Continued)

(52) U.S. Cl.
CPC ........ *H02H 3/085* (2013.01); *A61M 16/1095* (2014.02); *H02H 5/047* (2013.01);
(Continued)

(58) Field of Classification Search
CPC .................. A61M 16/1095; A61M 2205/3368
See application file for complete search history.

(56) References Cited

U.S. PATENT DOCUMENTS

| 2002/0083947 A1* | 7/2002 | Seakins | ................ H02H 1/0015 128/204.17 |
| 2006/0001433 A1* | 1/2006 | Bouton | ............. A61M 16/1095 324/536 |

(Continued)

*Primary Examiner* — Jared Fureman
*Assistant Examiner* — Christopher J Clark
(74) *Attorney, Agent, or Firm* — MUNCY, GEISSLER, OLDS & LOWE, P.C.

(57) ABSTRACT

A heating loop protective circuit, a respiration heating circuit and respiration aiding equipment are provided, wherein the heating loop protective circuit is connected to a heating loop and includes an acquisition sub-circuit, a suppression sub-circuit, a protective sub-circuit and a discharge sub-circuit; the acquisition sub-circuit collects input voltage of the protective sub-circuit and sends the input voltage to the suppression sub-circuit; the suppression sub-circuit clamps the input voltage and releases current through the discharge sub-circuit; and the protective sub-circuit performs short-circuit protection when the current is too high. In the present disclosure, the over-voltage protection is realized through the voltage clamp in such a manner of monitoring the voltage of the heating loop and suppressing the input voltage through the suppression sub-circuit, and
(Continued)

then the over-current protection is realized through the protective sub-circuit when the circuit current is too high.

10 Claims, 2 Drawing Sheets

(51) Int. Cl.
    *H02H 5/04*     (2006.01)
    *H02H 9/04*     (2006.01)

(52) U.S. Cl.
    CPC . *A61M 2205/3368* (2013.01); *A61M 2205/60* (2013.01); *H02H 9/041* (2013.01); *H02H 9/042* (2013.01)

(56) References Cited

U.S. PATENT DOCUMENTS

2009/0109591 A1\*    4/2009   Li .......................... H02H 9/042
                                                                   361/104
2019/0290866 A1\*    9/2019   Vos ........................ G01K 13/02

\* cited by examiner

HEATING LOOP PROTECTIVE CIRCUIT, RESPIRATION HEATING CIRCUIT AND RESPIRATION AIDING EQUIPMENT

TECHNICAL FIELD

The present disclosure relates to the field of respiration equipment, in particular to a heating loop protective circuit, a respiration heating circuit and respiration aiding equipment.

BACKGROUND

The existing respiration aiding equipment (such as a respirator) is usually provided with a variety of pipelines, and each pipeline is provided with an identification element and a temperature detection circuit. The respiration aiding equipment identifies pipeline information through the identification element, and temperatures of an air inlet and an air outlet of the pipeline are detected through the temperature detection circuit, and then the corresponding respiration working mode is carried out.

However, due to reversely or wrongly connected circuit or high instantaneous voltage when powering on and other situations, a heating loop of the existing respiration aiding equipment will occur leakage touch spark during use, resulting in a great safety risk.

Therefore, the prior art still needs to be improved and enhanced.

SUMMARY

In view of the above shortcomings of prior art, the purpose of the present disclosure is to provide a heating loop protective circuit, a respiration heating circuit and respiration aiding equipment. The over-voltage protection is realized through the voltage clamp in such a manner of monitoring the voltage of the heating loop and suppressing input voltage through a suppression sub-circuit, and then the over-current protection is realized through the protective sub-circuit when the circuit current is too high, thereby avoiding the safety risk caused by instantaneous high voltage touched electric spark.

In order to achieve the above purpose, the present disclosure adopts the technical solution below:

The present disclosure provides a heating loop protective circuit, which is connected to a heating loop, and the heating loop protective circuit includes an acquisition sub-circuit, a suppression sub-circuit, a protective sub-circuit and a discharge sub-circuit; the acquisition sub-circuit collects input voltage of the protective sub-circuit and sends the input voltage to the suppression sub-circuit; the suppression sub-circuit clamps the input voltage and releases current through the discharge sub-circuit; and the protective sub-circuit performs short-circuit protection when the current is too high.

The acquisition sub-circuit includes a first diode, a second diode and a third diode; an input end of the first diode, an input end of the second diode and an input end of the third diode are connected to the protective sub-circuit, and collect first input voltage, second input voltage and third input voltage respectively; and an output end of the first diode, an output end of the second diode and an output end of third diode are connected to the suppression sub-circuit.

The protective sub-circuit includes:
a first protective unit for performing short-circuit protection on a heating wire;
a second protective unit for performing short-circuit protection on a temperature detection module of the heating loop;
a third protective unit for performing short-circuit protection on the discharge sub-circuit;
one end of the first protective unit is connected to an input end of the heating wire, and the other end of the first protective unit is accessed to a first power source, one end of the second protective unit is connected to the acquisition sub-circuit and accessed to input voltage, the other end of the second protective unit is connected to the temperature detection module and an identification module of the heating loop, one end of the third protective unit is connected to the suppression sub-circuit, and the other end of the third protective unit is connected to the discharge sub-circuit.

The second protective unit includes a first protective tube, a second protective tube and a third protective tube; one end of the first protective tube is connected to the input end of the first diode and accessed to the first input voltage; the other end of the first protective tube is connected to the temperature detection module; one end of the second protective tube is connected to the input end of the second diode and accessed to the second input voltage; the other end of the second protective tube is connected to the temperature detection module; one end of the third protective tube is connected to the input end of third diode and accessed to the third input voltage; and the other end of the third protective tube is connected to the identification module.

The suppression sub-circuit includes a transient voltage suppressor, a cathode end of the transient voltage suppressor is connected to an output end of the first diode, an output end of the second diode and an output end of the third diode, and an anode end of the transient voltage suppressor is connected to one end of the third protective unit.

The discharge sub-circuit includes a fourth diode, a first resistance and a first switch tube, an input end of the fourth diode is accessed into control voltage, an output end of the fourth diode is connected to one end of the first resistance and a control end of the first switch tube, an input end of the first switch tube is connected to the third protective unit, and an output end of the first switch tube is connected to the other end of the first resistance and grounded.

The heating loop protective circuit further includes a temperature detection sub-circuit, which is accessed to a second power source, and an output end of the temperature detection sub-circuit is grounded.

Based on the above heating loop protective circuit, the present disclosure further provides a respiration heating circuit, including a heating loop and a heating loop protective circuit described above, the heating protective circuit is connected to the heating loop, and when a short circuit occurs to the heating loop, the heating circuit performs the short-circuit protection.

The heating loop includes a heating wire, a first temperature detection device, a second temperature detection device, a third temperature detection device and an identification module; an input end of the heating wire is connected to the protective sub-circuit, an output end of the heating wire is connected to a cathode of the first power source, one end of the first heating device, one end of the second temperature detection device and an IO port of the identification module are connected to the protective sub-circuit, and the other end of the first temperature detection device, the other end of the second temperature detection device and a grounding end of the identification module are connected to an input end of the suppression sub-circuit and the protective sub-circuit.

Based on the above respiration heating circuit, the present disclosure further provides respiration aiding equipment, including an equipment main body, a circuit board is arranged in the equipment main body, and the respiration heating circuit described above is arranged on the circuit board.

Compared with the prior art, the heating loop protective circuit provided by the present disclosure is connected to the heating loop, and the heating loop protective circuit includes the acquisition sub-circuit, the suppression sub-circuit, the protective sub-circuit and the discharge sub-circuit; the acquisition sub-circuit collects the input voltage of the protective sub-circuit and sends the input voltage to the suppression sub-circuit; the suppression sub-circuit clamps the input voltage and releases current through the discharge sub-circuit; and the protective sub-circuit performs short-circuit protection when the current is too high. In the present disclosure, the over-voltage protection is realized through the voltage clamp in such a manner of monitoring the voltage of the heating loop and suppressing the input voltage through the suppression sub-circuit, and then the over-current protection is realized through the protective sub-circuit when the circuit current is too high, thereby avoiding the safety risk caused by instantaneous high voltage touched electric spark.

DETAILED DESCRIPTION OF THE EMBODIMENTS

The present disclosure provides a heating loop protective circuit, a respiration heating circuit and respiration aiding equipment. The over-voltage protection is realized through the voltage clamp in such a manner of monitoring the voltage of the heating loop and suppressing the input voltage through the suppression sub-circuit, and then the over-current protection is realized through the protective sub-circuit when the circuit current is too high, thereby avoiding the safety risk caused by instantaneous high voltage touched electric spark.

The specific implementation mode of the present disclosure is convenient for a more detailed description made for the technical concept of the present disclosure, the solved technical problem, technical characteristics constituting the technical solution and the brought technical effects. It is noted that the explanation for these implementation modes does not constitute limitations to the protection scope of the present disclosure. In addition, the technical characteristics involved in the implementation mode below may be combined mutually as long as not constituting a conflict.

Figure 1:
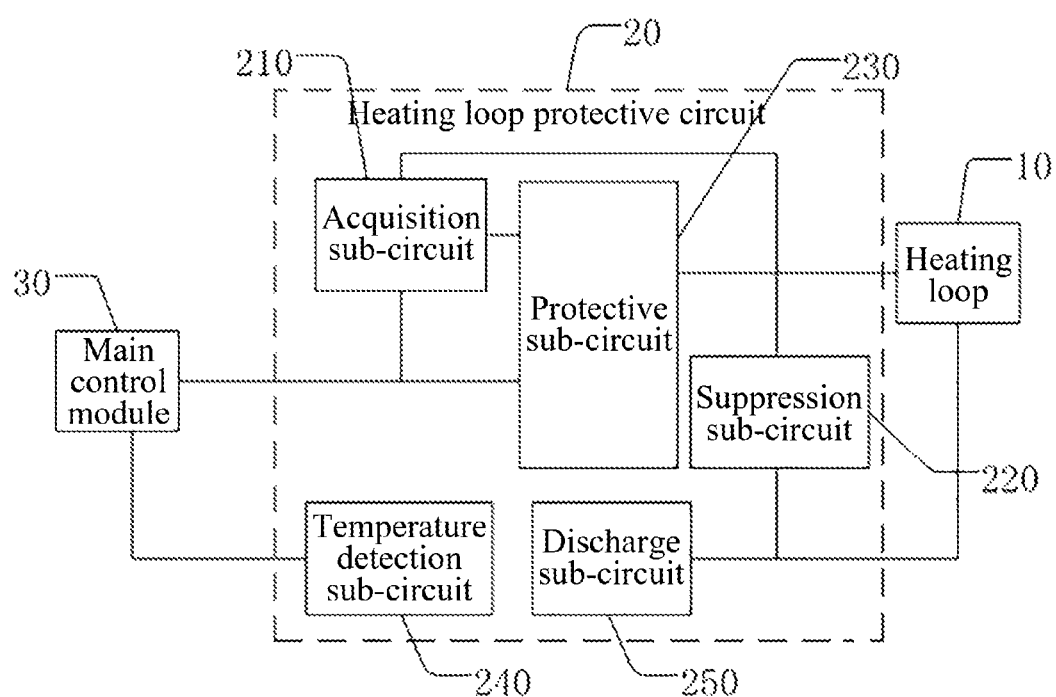
FIG. 1 is a structure block diagram of a heating loop protective circuit provided by the present disclosure.

In view of the problems of the prior art, please refer to FIG. 1, a heating loop protective circuit 20 provided by the present disclosure is configured to connect to a heating loop 10, and the heating loop protective circuit 20 includes an acquisition sub-circuit 210, a suppression sub-circuit 220, a protective sub-circuit 230 and a discharge sub-circuit 240. The heating loop 10 is generally supplied with power and controlled through the main control module 30, and the main control module 30 may be a main control chip of the respiration aiding equipment or an externally connected main control circuit and not limited herein. The heating loop protective circuit 20 is arranged between the main control module 30 and the heating loop 10, so as to avoid the safety risk of the heating loop 10 caused by instantaneous high voltage touched electric spark.

Figure 2:
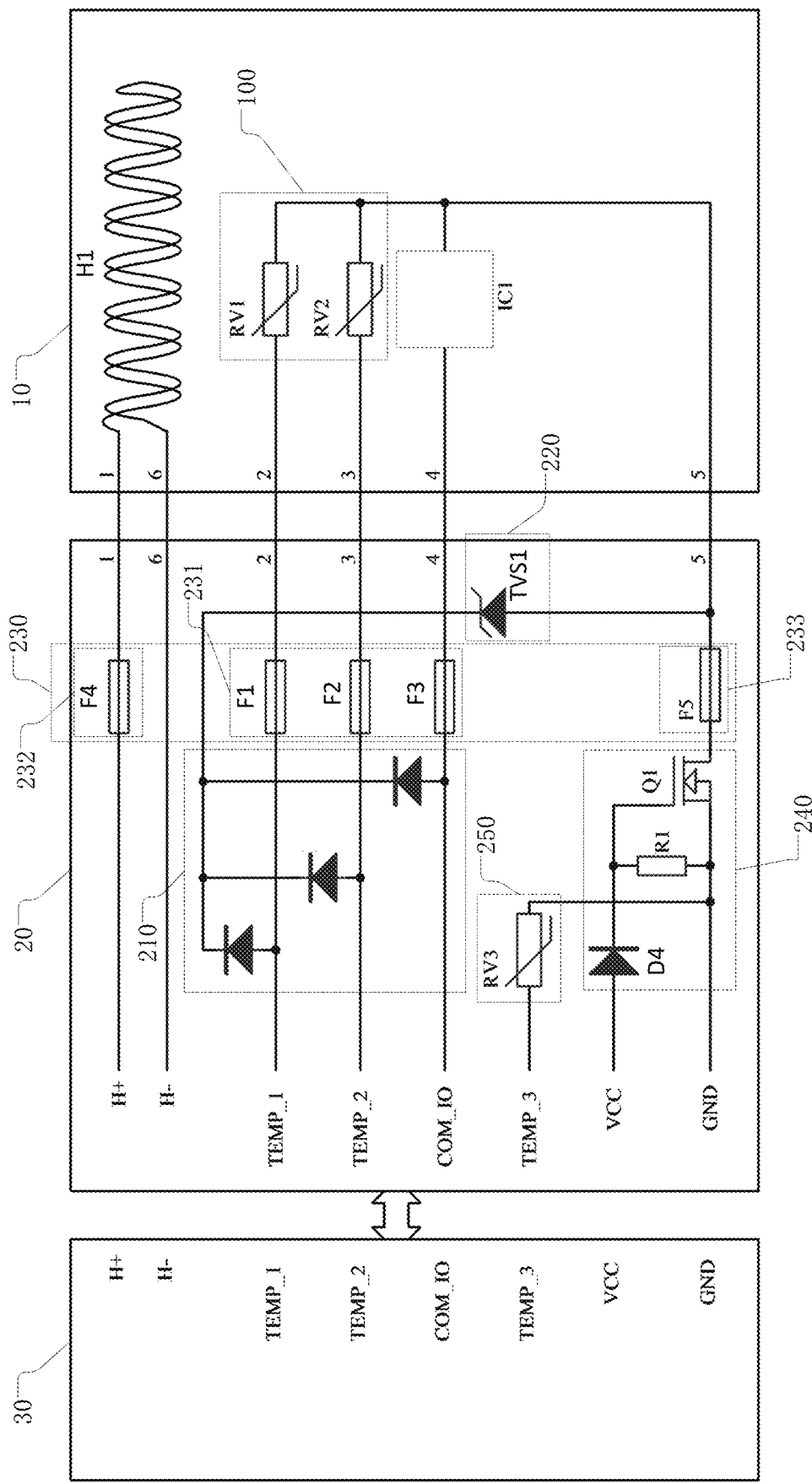
FIG. 2 is a circuit diagram of a respiration heating circuit provided by the present disclosure.

Specifically, please refer to FIG. 2, the acquisition sub-circuit 210 collects input voltage of the protective sub-circuit 230 and sends the input voltage to the suppression sub-circuit 220; the suppression sub-circuit 220 clamps the input voltage and releases current through the discharge sub-circuit 240; and the protective sub-circuit 230 performs short-circuit protection when the current is too high. At the same time, this embodiment realizes voltage clamp protection and over-current protection, so that the heating loop 10 avoids high voltage, and realizes the over-current protection function.

Specifically, please still refer to FIG. 2, the acquisition sub-circuit 210 includes a first diode D1, a second diode D2 and a third diode D3; an input end of the first diode D1, an input end of the second diode D2 and an input end of the third diode D3 are connected to the protective sub-circuit 230, and collect first input voltage, second input voltage and third input voltage respectively; and an output end of the first diode D1, an output end of the second diode D2 and an output end of third diode D3 are connected to the suppression sub-circuit 220.

During the specific implementation, in this embodiment, the existing heating loop 10 generally includes a plurality of IO ports, which supply power to the heating wire H1, the temperature detection device and the like respectively, or communicate with the identification module IC1, and this embodiment takes six IO ports as examples for explanation. Specifically, a first IO port is accessed into the anode of the first power source so as to supply power to the heating wire H1; a second IO port is connected to a cathode of the first power source, so that the heating wire H1 is formed with a loop; the first input voltage supplies power to the first temperature detection device RV1 through a third IO port; the second input voltage supplies power to the second temperature detection device RV2 through a fourth IO port; the third input voltage communicates with the identification module IC1 through a fifth IO port; and a sixth IO port is configured to enable the temperature detection device and the identification module IC1 to ground. When the heating loop 10 is powered on, voltage values of the third IO port, the fourth IO port and the fifth IO port are respectively connected through the first diode D1, the second diode D2 and the third diode D3 and output to the suppression sub-circuit 220, and voltage clamp is realized through the suppression sub-circuit 220, so that a backward heating loop 10 is not burned even the power-on instantaneous voltage is too high, and electric spark is not produced.

Further, please still refer to FIG. 2, the protective sub-circuit 230 includes a first protective unit for performing short-circuit protection on the heating wire H1, a second protective unit for performing short-circuit protection on the temperature detection module 100 of the heating loop 10, and a third protective unit for performing short-circuit protection on the discharge sub-circuit 240; one end of the first protective unit is connected to the input end of the heating wire H1, the other end of the first protective unit is accessed to the first power source, one end of the second protective unit is connected to the acquisition sub-circuit 210 and accessed to the input voltage, the other end of the second protective unit is connected to the temperature detection module 100 and the identification module IC1 of the heating loop 10, one end of the third protective unit is connected to the suppression sub-circuit 220, and the other end of the third protective unit is connected to the discharge sub-circuit 240.

During the specific implementation, in this embodiment, the heating wire H1 is subjected to the over-current protection through the first protective unit, when the current is too high, the loop of the heating wire H1 is disconnected through the first protective unit, so that the heating wire H1 is powered off, thereby achieving the effect of over-current protection.

Specifically, please still refer to FIG. 2, the first protective unit 232 includes a fourth protective tube F4, one end of the fourth protective tube F4 is connected to an input end of the heating wire H1, and the other end of the fourth protective tube F4 is connected to the anode of the first power source.

Further, please still refer to FIG. 2, the second protective unit 231 includes a first protective tube F1, a second protective tube F2 and a third protective tube F3; one end of the first protective tube F1 is connected to the input end of the first diode D1 and accessed to the first input voltage; the other end of the first protective tube F1 is connected to the temperature detection module 100; one end of the second protective tube F2 is connected to the input end of the second diode D2 and accessed to the second input voltage; the other end of the second protective tube F2 is connected to the temperature detection module 100; one end of the third protective tube F3 is connected to the input end of third diode D3 and accessed to the third input voltage; and the other end of the third protective tube F3 is connected to the identification module IC1.

Further, please still refer to FIG. 2, the third protective unit 233 includes a fifth protective tube F5, one end of the fifth protective tube F5 is connected to an anode end of the suppression sub-circuit 220, the temperature detection module 100 and the identification module IC1, and the other end of the fifth protective tube F5 is connected to the discharge sub-circuit 240.

The first protective tube F1, the second protective tube F2, the third protective tube F3, the fourth protective tube F4 and the fifth protective tube F5 are fused when the current is great, so as to disconnect the loop and realize the purpose of over-current protection.

Specifically, please still refer to FIG. 2, the suppression sub-circuit 220 includes a transient voltage suppressor TVS1, a cathode end of the transient voltage suppressor TVS1 is connected to the output end of the first diode D1, the output end of the second diode D2 and the output end of the third diode D3, and an anode end of the transient voltage suppressor TVS1 is connected to one end of the third protective unit.

Specifically, in this embodiment, the transient voltage suppressor TVS1 respectively receives voltage collected from the first diode D1, the second diode D2 and the third diode D3, the voltage is kept at a preset value, a three-circuit current is output to the fifth protective tube F5 and output to the discharge sub-circuit 240 through the fifth protective tube F5, and the current is discharged to ground through the discharge sub-circuit 240. It is noted that the preset value of the clamp voltage of the transient voltage suppressor TVS1 may be set according to needs, and it is not limited herein.

Further, please still refer to FIG. 2, the discharge sub-circuit 240 includes a fourth diode D4, a first resistance R1 and a first switch tube Q1, an input end of the fourth diode D4 is accessed into control voltage, an output end of the fourth diode D4 is connected to one end of the first resistance R1 and a control end of the first switch tube Q1, an input end of the first switch tube Q1 is connected to the third protective unit, and an output end of the first switch tube Q1 is connected to the other end of the first resistance R1 and grounded.

During the specific implementation, in this embodiment, a second power source accessed through the fourth diode D4 is output to the control end of the first switch tube Q1, the first switch tube Q1 is a NMOS tube, therefore the control end of the first switch tube Q1 is a grid electrode, the input end of the first switch tube Q1 is a drain electrode/source electrode of the NMOS tube, and the output end of the first switch tube Q1 is the source electrode/drain electrode of the NMOS tube. In this embodiment, the current accessed by the input end of the first switch tube Q1 is discharged to the ground by the output end of the first switch tube Q1, thereby realizing the normal current discharge. Optionally, the first switch tube may be a PMOS tube or a triode and the like, which only need to realize the current discharge function, and are limited herein.

Further, please still refer to FIG. 2, the heating loop protective circuit 20 further includes a temperature detection sub-circuit 250, which is accessed to the second power source, and an output end of the temperature detection sub-circuit 250 is grounded. Specifically, the temperature detection sub-circuit 250 includes a third temperature detection device RV3, and the temperature detection of the heating loop protective circuit 20 is realized by the third temperature detection device RV3. When the temperature is too high, the power failure is controlled through the main control module 30, so as to avoid losing the protective effect due to high temperature of the heating loop protective circuit 20.

It is noted that the first temperature detection device RV1, the second temperature detection device RV2 and the third temperature detection device RV3 may be temperature sensors, thermistors and the like, which are not limited herein.

Based on the above heating loop protective circuit 20, please still refer to FIG. 2, the present disclosure further provides a respiration heating circuit, including a heating loop 10 and a heating loop protective circuit 20 described above, the heating protective circuit is connected to the heating loop 10, and when a short circuit occurs to the heating loop 10, the heating loop 10 performs the short-circuit protection.

Specifically, please still refer to FIG. 2, the heating loop 10 includes a heating wire H1, a first temperature detection device RV1, a second temperature detection device RV2, a third temperature detection device RV3 and an identification module IC1; an input end of the heating wire H1 is connected to the protective sub-circuit 230, an output end of the heating wire H1 is connected to a cathode of a first power source, one end of the first heating device, one end of the second temperature detection device RV2 and an IO port of the identification module IC1 are connected to the protective sub-circuit 230, and the other end of the first temperature detection device RV1, the other end of the second temperature detection device RV2 and a grounding end of the identification module IC1 are connected to an input end of the suppression sub-circuit 220 and the protective sub-circuit 230. The identification module is specifically an identification chip, which can store temperature data detected by the temperature detection module and upload the temperature data required by the main control module.

During the specific implementation, in this embodiment, the acquisition sub-circuit 210 collects input voltage of the protective sub-circuit 230 and sends the input voltage to the suppression sub-circuit 220; the suppression sub-circuit 220 clamps the input voltage and releases current through the discharge sub-circuit 240; and the protective sub-circuit 230 performs short-circuit protection when the current is too high. At the same time, this embodiment realizes voltage clamp protection and over-current protection, so that the heating loop 10 avoids high voltage, and realizes over-current protection function, thereby avoiding the safety risk caused by instantaneous high voltage touched electric spark. The heating loop protective circuit 20 has been described in details above, so it will not be repeated herein.

Based on the above respiration heating circuit, the present disclosure further provides respiration aiding equipment, including an equipment main body, a circuit board is arranged in the equipment main body, and the respiration heating circuit described above is arranged on the circuit board. The respiration heating circuit has been described in details above, so it will not be repeated herein.

In conclusion, the heating loop protective circuit provided by the present disclosure is connected to the heating loop, and the heating loop protective circuit includes the acquisition sub-circuit, the suppression sub-circuit, the protective sub-circuit and the discharge sub-circuit; the acquisition sub-circuit collects the input voltage of the protective sub-circuit and sends the input voltage to the suppression sub-circuit; the suppression sub-circuit clamps the input voltage and releases current through the discharge sub-circuit; and the protective sub-circuit performs short-circuit protection when the current is too high. In the present disclosure, the over-voltage protection is realized through the voltage clamp in such a manner of monitoring the voltage of the heating loop and suppressing the input voltage through the suppression sub-circuit, and then the over-current protection is realized through the protective sub-circuit when the circuit current is too high, thereby avoiding the safety risk caused by instantaneous high voltage touched electric spark.

It is understood that those of ordinary skill in the art can make equivalent replacements or changes according to the technical solution and its inventive concept. However, these changes or replacement fall in the protection scope of the claims of the present disclosure.

What is claimed is:

1. A heating loop protective circuit connecting to a heating loop, comprising an acquisition sub-circuit, a suppression sub-circuit, a protective sub-circuit and a discharge sub-circuit; the acquisition sub-circuit collects at least one input voltage of the protective sub-circuit and sends the at least one input voltage to the suppression sub-circuit; the suppression sub-circuit clamps the at least one input voltage and releases current through the discharge sub-circuit; and the protective sub-circuit performs short-circuit protection when the current is too high;
   wherein the acquisition sub-circuit comprises a plurality of diodes, input ends of the plurality of diodes are connected to the protective sub-circuit, and output end of the plurality of diodes are connected to the suppression sub-circuit.

2. The heating loop protective circuit according to claim 1, wherein the plurality of diodes of the acquisition sub-circuit comprises a first diode, a second diode and a third diode; an input end of the first diode, an input end of the second diode and an input end of the third diode are connected to the protective sub-circuit, and collect first input voltage, second input voltage and third input voltage respectively; and an output end of the first diode, an output end of the second diode and an output end of third diode are connected to the suppression sub-circuit.

3. The heating loop protective circuit according to claim 2, wherein the protective sub-circuit comprises:
   a first protective unit for performing short-circuit protection on a heating wire;
   a second protective unit for performing short-circuit protection on a temperature detection module of the heating loop;
   a third protective unit for performing short-circuit protection on the discharge sub-circuit;
   one end of the first protective unit is connected to an input end of the heating wire, the other end of the first protective unit is accessed to a first power source, one end of the second protective unit is connected to the acquisition sub-circuit and accessed to the first, second, and third input voltage, the other end of the second protective unit is connected to a temperature detection module and an identification module of the heating loop, one end of the third protective unit is connected to the suppression sub-circuit, and the other end of the third protective unit is connected to the discharge sub-circuit.

4. The heating loop protective circuit according to claim 3, wherein the second protective unit comprises a first protective device, a second protective device and a third protective device; one end of the first protective device is connected to an input end of the first diode and accessed to the first input voltage; the other end of the first protective device is connected to the temperature detection module; one end of the second protective device is connected to an input end of the second diode and accessed to the second input voltage; the other end of the second protective device is connected to the temperature detection module; one end of the third protective device is connected to an input end of third diode and accessed to the third input voltage; and the other end of the third protective device is connected to the identification module.

5. The heating loop protective circuit according to claim 4, wherein the suppression sub-circuit comprises a transient voltage suppressor, a cathode end of the transient voltage suppressor is connected to an output end of the first diode, an output end of the second diode and an output end of the third diode, and an anode end of the transient voltage suppressor is connected to one end of the third protective unit.

6. The heating loop protective circuit according to claim 3, wherein the discharge sub-circuit comprises a fourth diode, a first resistance and a first switch device, an input end of the fourth diode is accessed into control voltage, an output end of the fourth diode is connected to one end of the first resistance and a control end of the first switch device, an input end of the first switch device is connected to the third protective unit, and an output end of the first switch device is connected to the other end of the first resistance and grounded.

7. The heating loop protective circuit according to claim 1, wherein the heating loop protective circuit further comprises a temperature detection sub-circuit, which is accessed to a second power source, and an output end of the temperature detection circuit is grounded.

8. A respiration heating circuit, comprising a heating loop protective circuit according to claim 1, the heating protective circuit is connected to a heating loop, and when a short circuit occurs to the heating loop, the heating circuit performs the short-circuit protection.

9. The respiration heating circuit according to claim 8, wherein the heating loop comprises a heating wire, a first temperature detection device, a second temperature detection device, and an identification module; an input end of the heating wire is connected to the protective sub-circuit, an output end of the heating wire is connected to a cathode of a first power source, one end of the first temperature detection device, one end of the second temperature detection device and an IO port of an identification module are connected to the protective sub-circuit, and the other end of the first temperature detection device, the other end of the second temperature detection device and a grounding end of the identification module are connected to an input end of the discharge sub-circuit and the protective sub-circuit.

10. Respiration aiding equipment, comprising an equipment main body, a circuit board is arranged in the equipment main body, and a respiration heating circuit described in claim 8 is arranged on the circuit board.

\* \* \* \* \*